United States Patent [19]

Pike

[11] 4,031,889

[45] June 28, 1977

[54] POWER OPERATED ASPIRATING HYPODERMIC SYRINGE

[76] Inventor: William Floyd Pike, 915 Alamosa, Carlsbad, N. Mex. 88220

[22] Filed: May 19, 1976

[21] Appl. No.: 687,893

Related U.S. Application Data

[63] Continuation-in-part of Ser. No. 559,961, March 25, 1975, Pat. No. 3,977,401, and a continuation-in-part of Ser. No. 593,771, July 14, 1975, Pat. No. 3,977,402.

[52] U.S. Cl. .............................. 128/215; 128/218 A
[51] Int. Cl.[2] .......................................... A61M 5/00
[58] Field of Search .... 128/218 R, 218 D, 218 DA, 128/218 M, 218 A, 218 F, 215, 216, 220, 221, 218 N, 218 NV, 173 H, 224, 213, 276

[56] References Cited

UNITED STATES PATENTS

| | | | |
|---|---|---|---|
| 2,655,919 | 10/1953 | Goodstein et al. | 128/218 M |
| 2,960,087 | 11/1960 | Uytenbogaart | 128/218 F |
| 3,055,362 | 9/1962 | Uytenbogaart | 128/218 F |
| 3,066,670 | 12/1962 | Stauffer | 128/218 F |
| 3,527,212 | 9/1970 | Clark | 128/215 X |
| 3,688,765 | 9/1972 | Gasaway | 128/173 H |

*Primary Examiner*—John D. Yasko
*Attorney, Agent, or Firm*—Henry Heyman

[57] ABSTRACT

A self-contained apparatus which facilitates intramuscular or subcutaneous injection of medications is disclosed herein. All components normally required for such injections, i.e., antiseptic, antiseptic applicator, hypodermic needle of appropriate length and gauge, and unit dose of injectable medication are maintained under sterile conditions within subject invention. The apparatus, in a preferred embodiment, contains a single compressed gas cartridge which when ruptured provides power to: (1) sever retention shear tabs of a slidable injection assembly, (2) propel said slidable injection assembly from a storage position to an operating position, (3) couple one end of a double-ended hypodermic needle with the unit dose of medication, (4) insert the other end of said double-ended hypodermic needle into tissues, (5) automatically effect controlled aspiration, (6) expel the medication into tissues of the injection site, and (7) indicate the site of injection as well as the type of medication used. An alternate means of automatically effecting aspiration in subject invention is also disclosed herein.

7 Claims, 15 Drawing Figures

POWER OPERATED ASPIRATING HYPODERMIC SYRINGE

BACKGROUND OF THE INVENTION

This application is a continuation-in-part of application Ser. No. 559,961, filed Mar. 25, 1975 by William F. Pike, titled "Injection Apparatus and Method" now U.S. Pat. No. 3,977,401 and a continuation-in-part of application Ser. No. 593,771 filed July 14, 1975 by William F. Pike titled "Injection Apparatus and Method with Automatic Aspiration Feature" now U.S. Pat. No. 3,977,402.

The present invention relates generally to disposable automatic hypodermic injection devices for use in effecting either intramuscular or subcutaneous injection of medications.

Recognition of the limitations of devices and techniques traditionally used for such injections has stimulated development of numerous imaginative automatic syringe designs in attempts to circumvent associated problems such as: (1) the risk of injection accidents, including accidental death, due to failure to aspirate, (2) the risk of localized or systemic infections subsequent to injection, and (3) the susceptibility of accident by inexpert health care specialists in administering parenteral medications. Also of great concern is inefficient utilization of the time of health care professionals due to the necessity of obtaining and using separate items in the injection process.

Although many attempts have been made to produce automatic devices to circumvent one or more of the above noted objections, the prior art devices have one or more deficiencies such as being unwieldy, heavy, unreliable, or too expensive to be used as disposable items. Most prior art automatic syringes are powered by multiple springs, bellows, electrical solenoids, or an exogenous source of compressed gas. Many require multiple control means and contain gears, screws, ratchets and other devices which add to their expense and susceptibility to failure in operation.

A few possess an automatic aspiration means which is essential to avoid accidental injection of medication into a blood vessel. Such prior art devices, in general, operate a suction function from contained vacuum chambers, electrical solenoid generation of a vacuum, or from an exogenous vacuum source. Deficiencies in such devices include: (1) dissipation of vacuum by leakage of air past seals while the devices are stored for future use, (2) mechanical or pneumatic complexity resulting in expensive manufacture and susceptibility of failure and (3) require successive manipulations in application leading to possible injection accidents due to operator error.

The present invention is an improvement over the prior art by virtue of containing under sterile conditions all components required for intramuscular or subcutaneous injection, including means for automatically generating vacuum sufficient for unfailing and controlled aspiration. The device of this invention renders aspiration and subsequent injection of medication automatic and uniform.

SUMMARY OF THE INVENTION

The present invention eliminates the objections and deficiencies of prior art devices. A principal objective of subject invention is to provide an economical, automatic and entirely self-contained hypodermic syringe. It is designed to contain under sterile conditions within a tubular container all components required to correctly perform such injections.

Included are antiseptic and antiseptic applicator to disinfect tissues at the injection site prior to injection and to maintain the state of disinfection during the injection process. Also included is a slidable injection assembly maintained in a selected position within a tubular housing until the device is activated. Said slidable injection assembly contains in a sealed capsule a prescribed injectable medication, preferably in unit dose form, a piston to discharge said medication, a hollow double-ended needle of appropriate length and gauge which provides means for conducting the medication into tissues, and an automatic aspiration mechanism. A single slidable and rupturable compressed gas cartridge in the tubular container provides motive power to: (1) sever retention shear tabs of a slidable injection assembly, (2) propel said slidable injection assembly from a storage position to an operating position, (3) couple one end of a double-ended hypodermic needle with the unit dose of medication, (4) insert the other end of said double-ended needle into tissues, (5) automatically effect controlled aspiration, (6) expel the medication into tissues of the injection site, and (7) indicate the site of injection as well as the medication used.

The object of indicating the site of injection is that there continues to be a significant problem with injection of medications into the same or a closely neighboring site by personnel on different duty shifts and, occasionally, by personnel on the same shift. This may result in needless additional pain for the patient, formation of sterile abscesses, mild to severe allergic reactions, and occasionally death.

The object of indicating the medication used is to ascertain by inspection that the medication injected was, in fact, that which was prescribed. Additionally, control of licit injectable narcotic substances is a major problem in hospitals and extended care institutions. This is made possible in large measure by the use of vials and ampules containing more than one dose of injectable medication and by the substitution of innocuous injectables, such as physiological saline, by professional staff.

Verification of the site and medication injected will reduce the number of acts and consequences previously described by providing single use means for identification.

The manner of accomplishing the above objectives will become apparent from reading the following specification in conjunction with the accompanying drawings in which.

DETAILED DESCRIPTION

Figure 1:
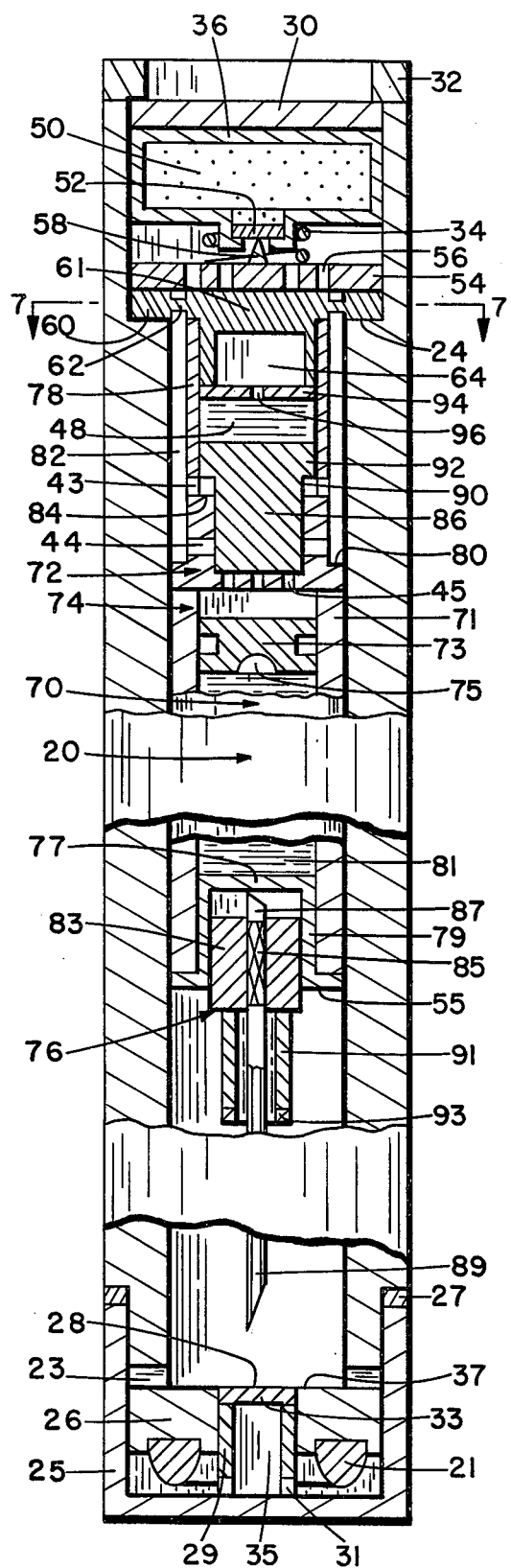
FIG. 1 is a side elevational view in cross section of the apparatus constituting the present invention.

Referring to FIG. 1, the hypodermic syringe of this invention includes a tubular housing 20 having a first end and a second end. The first end, also referred to as the "upper end", has a cylindrical relief in the inner wall which extends from the upper end of the housing to a shoulder 24 formed by the unrelieved adjacent portion of the housing 20. The second end, also referred to as the "lower end", is provided with a transverse end wall 26 possessing a central axial aperture 28 through which a hypodermic needle and injection indicator will pass as described subsequently.

The first end of housing 20 is hermetically sealed by flexible disc 30 and annular closure 32. Slidably supported in the housing and resting upon a spring 34 is compressed gas cartridge 36, containing compressed gas 50, and having a rupturable end wall membrane 52. The rupturable membrane is preferably a thin metallic disc easily penetrated by a sharp point by finger pressure.

Spring 34 is in turn supported by rigid disc 54 which is perforated by vents 56. Affixed to the upper surface of disc 54 is a pointed perforator 58, preferably serrated, whose point is in proximity with rupturable membrane 52.

Immediately below the structure thus far described are the movable elements of the aspiration, medication, and hypodermic subassemblies.

To the end that all movable parts will be retained in a selected storage position despite any extraneous externally applied forces prior to use, an injection assembly retention element 60 is provided. Element 60 is in the form of a cylindrical disc which is supported on shoulder 24 of the housing and is provided with weakening reliefs 62, also referred to as "shear tabs", to the end that when gas pressure is applied to closure element 61 shear tabs 62 will sever.

Injection assembly 70 refers to all the movable parts below retention element 60 and is comprised of three subassemblies: an automatic aspiration subassembly, indicated generally at 72, a medication subassembly, indicated generally at 74, and a hypodermic needle and injection indicator subassembly indicated generally at 76.

Components of aspiration subassembly 72 are contained within a cylindrical aspiration control housing 78, provided with an outwardly extending flange 80 at the bottom end. Excepting said flanged end, the diameter of aspiration control housing 78 is less than the internal diameter of tubular housing 20 thereby providing a passageway 82 through which compressed gas will pass in actual operation of subject invention. Shoulder portion 84 in aspiration control housing 78 provides, with the stem 90 of piston 86, a pneumatic ram and cylinder in which compressed gas 50 may act in displacing the control piston 86 by pressure against piston head 92, as described subsequently. Shoulder 84 may be integral with aspiration control housing 78 as shown or it may be incorporated in the form of a perforated sleeve in the same position within said housing. Ports in the slide wall of housing 78, viz., upper gas inlet 43 and lower gas inlet 44, provide means of selectively allowing entry of compressed gas 50 into the interior of injection assembly 70 for sequential automatic aspiration and medication injection as will be described in detail.

Aspiration control housing 78 is sealed at its upper end by closure element 61, the barrel extension of which is hermetically sealed to the inner wall of housing 78 and to a cover 94 which has a limiting orifice 96 to form a cavity 64. Cavity 64 is at atmospheric pressure during storage.

Hermetically sealed to housing 78 and shoulder 84 and supported by contact of its lower end with the internal base of housing 78 is a flanged aspiration control piston 86 which serves as valving means, said flanged portion 92 in position above upper gas inlet 43. Interposed between the upper surface of piston 86 and cover 94 and otherwise contained by housing 78 is liquid 48, preferably water, although a more viscous liquid may be employed. The base of aspiration control housing 78, sealingly engaged with medication subassembly 74 about its periphery, is provided with perforations 45 to allow gaseous communication between aspiration subassembly 72 and medication subassembly 74.

Tubular housing 20 and aspiration control housing 78 are preferably prepared from any suitable transparent polymer such as polycarbonate, polymethylpentene, or polyvinyl chloride.

Components of medication subassembly 74 are contained within medication cartridge 71, preferably composed of shatter-resistant glass, which may be lubricated to reduce friction between medication cartridge 71 and tubular housing 20 and hermetically sealed by means known in the art to the end that gas leakage between medication cartridge 71 and housing 20 is prevented during operation. Interposed between medication piston 73, which is provided with concavity 75, and septum 77 and otherwise contained by medication cartridge 71 is medication 81, preferably in unit dose form.

Housing 79, preferably a resilient inert polymer, is generally cylindrical with a flanged leading annular surface 55. Partially contained within housing 79 during storage is piston 83 of hypodermic needle and injection indicator subassembly 76. Piston 83, preferably a plastic cylinder, surrounds and supports knurled hypodermic needle 85, said needle being double-ended and having a sharpened upper end 87 and a sharpened lower end 89. Adjacent lower end 89 and attached to piston 83 is indicator support 91 to which is attached at its leading surface injection indicator 93 which is impregnated with visible and/or invisible chemical indicators or dyes which function in a manner to be described subsequently. Injection indicator 97 shown in FIG. 3, however, represents the preferred configuration and may be codably imprinted and is removable by adhesion to a patient's skin during injection, as described subsequently.

Surrounding aperture 28 and affixed in a diametric plane to the second end of the main housing is annular antiseptic applicator 21 which is impregnated with a suitable antiseptic such as isopropanol. Air escape ports 23 penetrate the side wall of housing 20 proximate transverse end wall 26 of the lower end.

Enclosing the lower end of housing 20, antiseptic applicator 21 and air escape ports 23 is a slidably removable and generally cylindrical antiseptic applicator cover 25, which is hermetically sealed before use of subject invention by adhesive 27 to insure sterility of the interior of housing 20 and to prevent evaporation of the antiseptic in antiseptic applicator 21. Centrally affixed to the base of antiseptic applicator cover 25 and projecting into and sealing aperture 28 before use is cylinder 29 having perforations 31 surmounted by septum 33 thereby providing a cavity 35.

Figure 2:
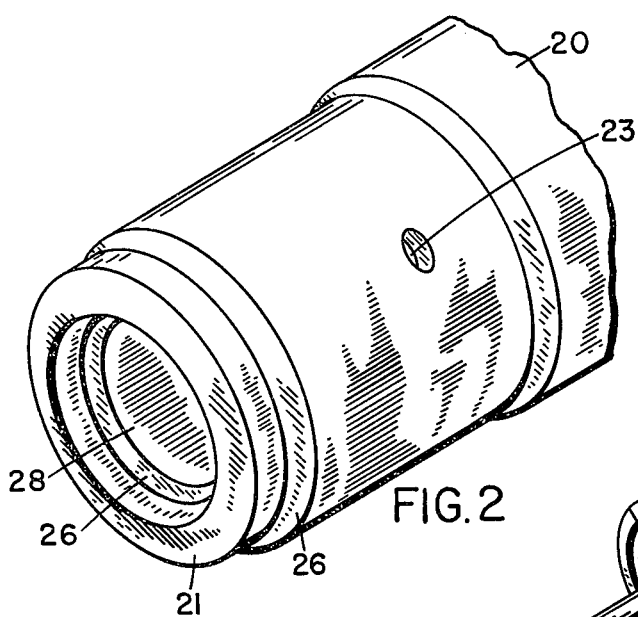
FIG. 2 is a fragmentary end view of the antiseptic applicator with cover removed.

FIG. 2 illustrates the external appearance, with antiseptic applicator cover 25 removed, of the lower end and a portion of tubular housing 20. In this FIGURE, the annular shape and elevated position of antiseptic applicator 21 is readily discerned. Aperture 28, through which lower end 89 of hypodermic needle 85 and the injection indicator 93 will pass are visible, as is one of the air escape ports 23.

Figure 4:
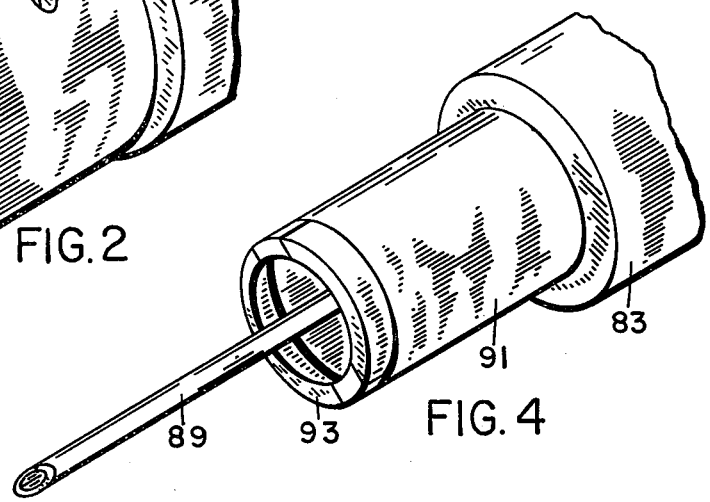
FIG. 4 is a fragmentary end view of the injection verification device of an alternative embodiment.
Figure 3:
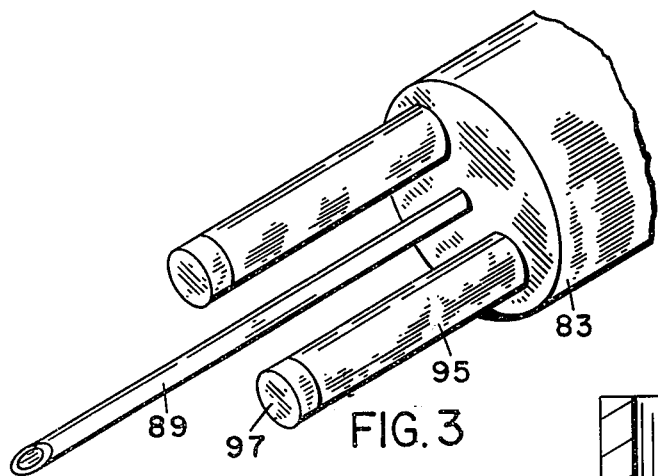
FIG. 3 is a fragmentary end view of the injection verification device of the preferred embodiment.

FIG. 3 is an end view of the preferred embodiment of the injection verification device. FIG. 4 depicts the appearance of another embodiment of the hypodermic needle and injection verification device.

Figure 5:
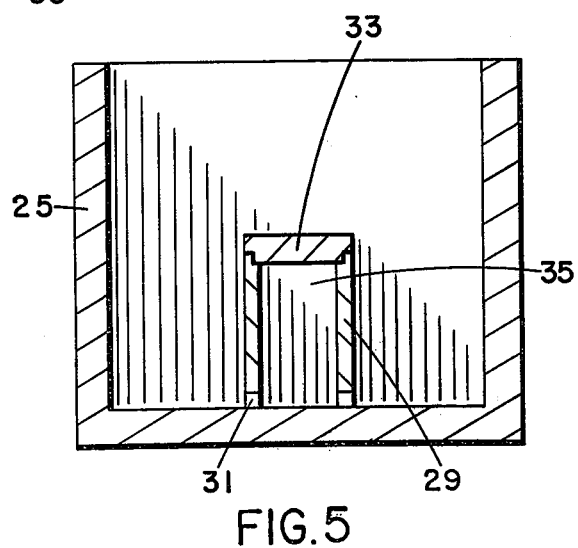
FIG. 5 is a cross sectional view of the antiseptic applicator cover.

FIG. 5 is an enlarged cross sectional view of the antiseptic applicator cap 25 whose additional function will be referred to in detail subsequently.

Figure 6:
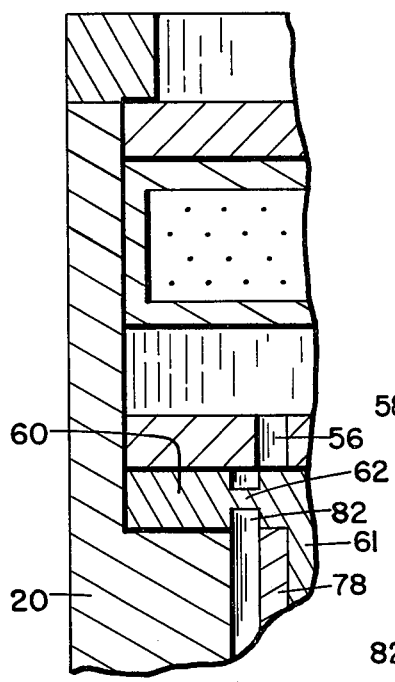
FIG. 6 is a fragmentary cross sectional view in great enlargement illustrating shear tab position.
Figure 7:
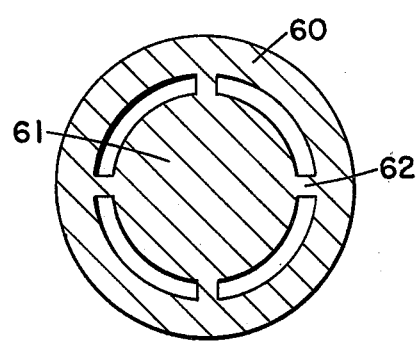
FIG. 7 is a transverse sectional view taken along the line 7—7 of FIG. 1 depicting position of shear tabs.

Attention is now directed to FIGS. 6 and 7. FIG. 6 is an enlarged fragmentary view which more clearly shows position of shear tabs 62. FIG. 7 is a transverse sectional view along the line 7—7 of FIG. 1 further illustrating the structure and location of shear tabs 62. Tubular housing 20 is not shown in this FIGURE.

Figure 8:
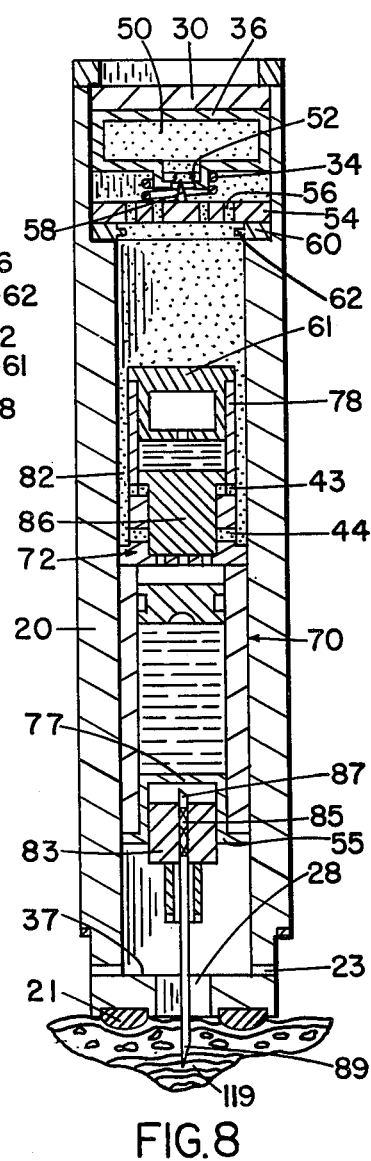
FIG. 8 is a side elevational view in cross section illustrating axial displacement of the injection assembly with needle penetration of tissues subsequent to perforation of the rupturable membrane in the compressed gas cartridge and shear of retention tabs.

Prior to injection antiseptic applicator cap 25 is removed. Antiseptic applicator 21 is rubbed over the skin and pressed against the skin immediately prior to injection to render the skin taut. When ready, the operator inserts a finger into the recess of the upper end of the housing thereby contacting flexible disc 30. In FIG. 8 flexible disc 30 has been manually depressed and released, in the process of which perforator 58 penetrated and ruptured membrane 52. Compressed gas cartridge 36 has been slidably returned to its original position by spring 34 thereby allowing compressed gas 50 to pass through vents 56 to apply pressure directly to cover 61 of aspiration subassembly 72 to sever shear tabs 62 and to propel injection assembly 70 axially towards the second end. As injection assembly 70 proceeds in said direction, air which has been entrapped below injection assembly 70 escapes through air escape ports 23 to allow unimpeded movement of injection assembly 70.

At this time lower end 89 of hypodermic needle 85 is passing through aperture 28 and initiating penetration of tissues 119 at the injection site. In this FIGURE the leading peripheral surface of piston 83 has not contacted housing tube base 37. Therefore upper end 87 of hypodermic needle 85 has not penetrated septum 77. Sharpened lower end 89 of hypodermic needle 85 does not exert sufficient force upon piston 83 during tissue penetration to initiate penetration of septum 77 by upper end 87. Unimpeded propellant gas 50 has entered gas passage 82, upper gas inlet 43, and lower gas inlet 44. Further penetration of propellant gas 50 is temporarily prevented by the presence of aspiration control piston 86 in housing 78. Additionally, complete displacement of injection assembly 70 through tubular housing 20 to its operating position occurs rapidly so that propellent gas 50 does not enter injection assembly 70.

Figure 9:
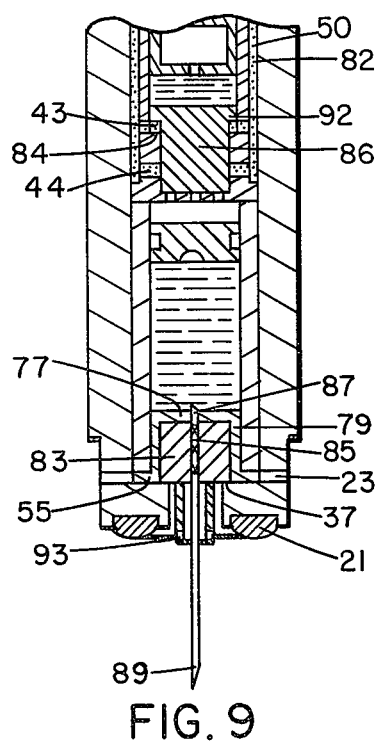
FIGS. 9, 10, 11, 12 are fragmentary cross sectional views depicting the sequence of events subsequent to maximum displacement of the injection assembly within its container.

Referring now to FIG. 9, maximum displacement of injection assembly 70 has taken place. The peripheral surface of piston 83 has contacted housing tube base 37, thereby forcing upper end 87 of hypodermic needle 85 to penetrate septum 77. The leading flange 55 of housing 79 has also contacted housing tube base 37, thereby closing air exhaust ports 23. Lower end 89 of hypodermic needle 85 has achieved desired depth of penetration of the tissues and injection indicator 93 has lightly pressed against the skin at the injection site thereby marking the site of injection.

In the preferred embodiment of the injection indicator or injection verification device shown in FIG. 3, the leading surface of an individual indicator 97 is provided with an annulus or disc which has been factory imprinted, color-coded, or rendered otherwise codably identifiable. One side of indicator 97, the side which is in contact with indicator support 95, is coated with a weak adhesive whereas the other side, i.e., the side which will contact the patient's skin, is coated with a hypoallergenic adhesive which has greater adhesiveness than said first adhesive. The result is that upon contact with the patient's skin, indicator 97 is transferred from support 95 to the patient's skin. No possibility of permanently marking the injection site exists nor is there any likelihood of inducing an allergic reaction.

In the alternate embodiment shown in FIG. 4, injection indicator 93 is one or more probes of absorbent material such as cotton which has been codably impregnated, using a low vapor pressure solvent such as glycerol, with one or more chemical substances which are visible in ordinary light and/or which fluoresce in a characteristic manner when exposed to ultraviolet or other electromagnetic radiation. A large number of chemical indicators for rendering an injection site detectable as described are available. It will be noted, particularly as shown in this FIGURE, that the injection indicator 93 is separated from possible contact with lower end 89 to prevent any dye from entering the skin puncture left by lower needle end 89 and becoming entrapped in subcutaneous tissues. The result of such entrapment might cause undesirable permanent marks at the injection site or allergic reactions.

Returning to FIG. 9, since injection assembly 70 has undergone maximum displacement and needle insertion essentially instantaneously, compressed gas 50 in gas passage 82, upper gas inlet 43 and lower gas inlet 44 has not yet begun urging aspiration control piston 86 axially upward in this FIGURE.

Figure 10:
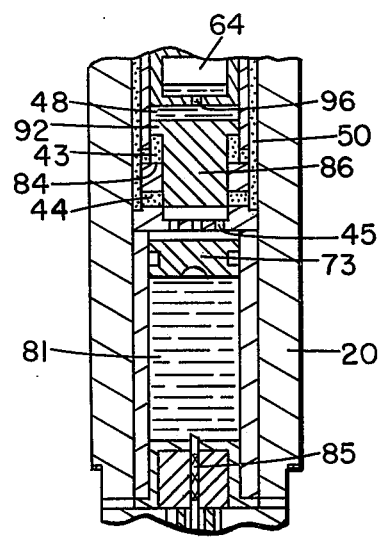

In FIG. 10, however, it will be noted that compressed gas 50 has exerted pressure for sufficient time on flange 92 of movable control piston 86 to initiate axial displacement towards the first end. The rate of said displacement is limited, however, by liquid 48 which is being forced through limiting orifice 96 into cavity 64 by control piston 86. As control piston 86 in displaced axially upward by compressed gas 50 it creates a partial vacuum behind it, communicating said vacuum through perforations 45 to medication piston 73 thereby displacing piston 73 upward and effecting automatic aspiration.

In the event that blood enters medication 81 during aspiration, hypodermic needle 85 is immediately withdrawn by pulling axially upward on tubular housing 20. Hypodermic needle lower end 89 is inserted through septum 33 of the antiseptic applicator cap, previously removed and shown in FIG. 5, and medication 81 is allowed to discharge, initially entering chamber 35, then flowing through perforations 31 into the major reservoir formed by antiseptic applicator cap 25. Discharge into the container means described above prevents production of undersirable and potentially dangerous aerosols.

Figure 11:
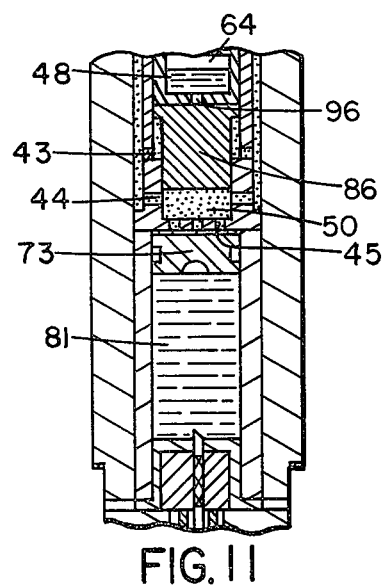

In FIG. 11, control piston 86 has achieved maximum axial displacement forcing nearly all of liquid 48 into cavity 64 through limiting orifice 96. Medication piston 73 has also undergone maximum displacement along the same axis. The base of control piston 86 has passed lower gas inlet 44 thereby premitting compressed gas 50 to enter and flow through perforations 45 to the upper surface of medication piston 73. Increased gas pressure on the upper surface of medication piston 73 initiates injection of medication 81 into the tissues.

Figure 12:
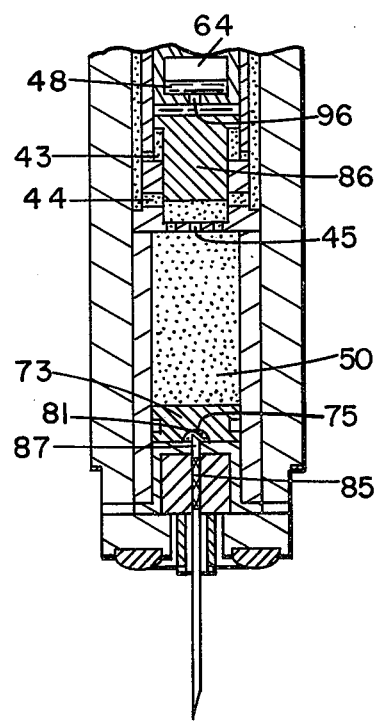

In FIG. 12, delivery of medication 81 through hypodermic needle 85 into the tissues has been completed through sustained gas pressure upon the upper surface of medication piston 73. Upper end 87 of needle 85 is enclosed by concavity 75, along with a minute amount of residual medication 81, thereby precluding the possibility of compressed gas 50 entering hypodermic needle 85. Therefore, no propellent gas can be injected into the tissues. In this FIGURE, it will also be noted that a reduction in gas pressure following injection permits gas compressed in cavity 64 by liquid 48 during aspiration to begin forcing liquid 48 in the reverse direction through orifice 96. The rate of return is limited, however, by limiting orifice 96.

Figure 13:
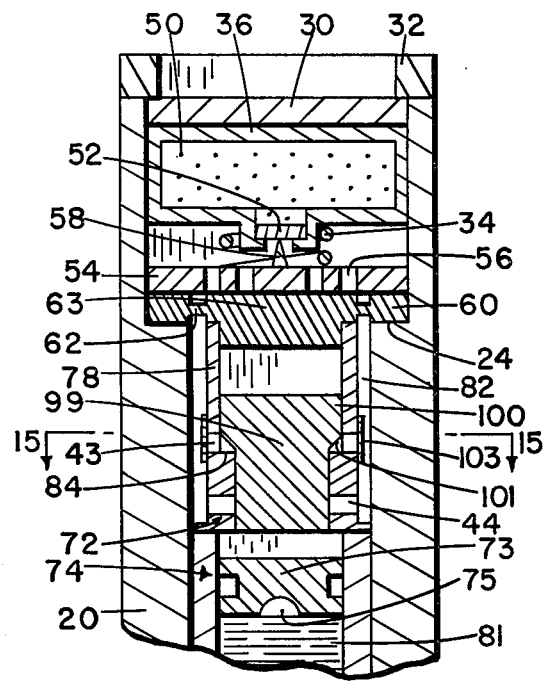
FIG. 13 is a fragmentary cross sectional view illustrating an alternate embodiment for effecting controlled automatic aspiration in subject invention.
Figure 14:
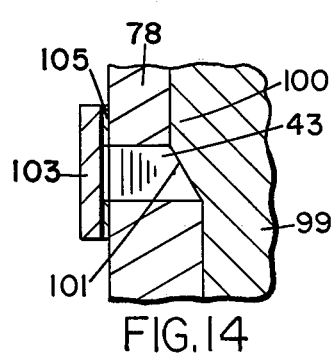
FIG. 14 is a fragmentary cross sectional view in great enlargement of the alternate embodiment for effecting automatic aspiration depicted in FIG. 13.

An alternate means for effecting controlled automatic aspiration in subject invention is shown in fragmentary cross section in FIG. 13. In this embodiment, unlike the embodiment of FIG. 1, there is no limiting orifice 96 and no liquid 48. Nor is there a base in aspiration control housing 78 upon which control piston 99 may rest. With reference to FIGS. 13 and 14, it will be seen that control piston 99 is tapered below the flange 100 with a surface 101 which supports it upon shoulder 84 of housing 78. Surface 101 additionally serves as the surface upon which compressed gas 50 acts in urging piston 99 axially upward. The structure which limits the rate of upward movement of control piston 99 and hence the rate of aspiration is limiting porous membrane 103, attached to housing 78 by means of adhesive 105 shown in FIG. 14, therefore limiting the rate of access of compressed gas 50 to upper gas inlet 43.

Figure 15:
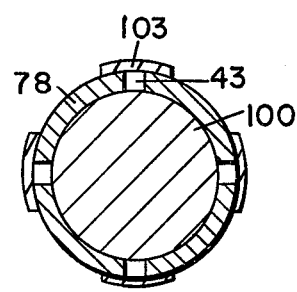
FIG. 15 is a transverse sectional view taken along the line 15—15 of FIG. 13.

FIG. 15, taken along the line 15—15 of FIG. 13, is a transverse cross section of automatic aspiration subassembly 72 showing one configuration of the alternate means, although the actual number of upper gas inlets 43 and limiting porous membranes 103 are not restricted in number to those shown but may be either fewer or more numerous. Adhesive 105 is not shown in FIGS. 15 or 17.

Membrane 103 may be composed of any selectively porous or permeable material. Preferred, however, are membranes in which the porosity is limited to about 15 nanometers per pore or less. This type of membrane is available commercially through such firms as Amicon, Gelman, Millipore, and Nuclepore, among others. They may be used singly, stacked collectively, or with separations between membranes in order to achieve the desired goal of selectively impeding compressed gas 50 such that the rate of upward axial displacement of piston 99 is precisely controlled, thereby controlling the rate of aspiration.

Concluding, it must be noted that although a major objective of subject invention is to provide a self-contained economical disposable hypodermic syringe, it is obvious that most components of subject invention may be used more than a single time provided the syringes are retained and returned to the supplier for factory sterilization and assembly, including replacement of components which cannot be recycled. It is also obvious that subject invention may be modified such that loading with disposable and sterile medication-containing cartridges is effected.

What is claimed is:

1. A disposable gas pressure operated hypodermic syringe for automatically inserting a hypodermic needle into tissue, drawing a vacuum in said needle, and finally injecting medicament into the tissue, comprising: an elongated tubular main housing having a sealed first end, being the triggering end, and a second end, being the needle end; a source of compressed gas housed in a first end portion of the main housing; an elongated unitary tube slidably supported in the main housing and extending from a first end which is proximate the source of compressed gas when the syringe is in the preset condition to a second end which is foreshortened from the second end of the main housing by the length of an extensible portion of the hypodermic needle, substantially; a sliding valve member having a cylindrical head and a cylindrical stem, said cylindrical stem having a diameter less than that of the head, said valve member cylindrical head having a hermetic fit in a reduced cross sectional portion of the elongated unitary tube, and the stem portion having a hermetic fit with a further reduced cross sectional portion of the elongated unitary tube, said sliding valve member being situated in the elongated unitary tube proximate the source of compressed gas; a medicament chamber support in the elongated unitary tube between the sliding valve member and the second end of said elongated unitary tube; a piston closing the end of the medicament chamber facing the sliding valve member; a hypodermic needle supported in the second end of the elongated unitary tube proximate the medicament chamber, said hypodermic needle having an elongated end portion housed in and facing the second end of the main housing; manual means for releasing the compressed gas into the first end of the main housing to propel the elongated unitary tube to the second end of the main housing and to insert the elongated end portion of the hypodermic needle into tissue; means for admitting gas pressure to the head of the sliding valve member on the side facing the medicament chamber, means for restricting the movement of the sliding valve member to a selected rate of travel, the movement of the stem of said sliding valve producing a vacuum in the medicament chamber thereby effecting the function of aspirating, means controlled by the sliding valve member when it has completed the aspiration stroke, substantially, for admitting gas pressure into the medicament chamber to inject the medicament into tissue.

2. The device of claim 1 in which the means for admitting gas pressure to the sliding valve member is a first port through the wall of the elongated unitary tube at a position adjacent the head of the sliding valve member on the stem side when said sliding valve member is in the preset condition, and the means for admitting gas pressure into the medicament chamber is a second port through the wall of the elongated unitary tube at a position uncovered by the sliding valve stem when the sliding valve has completed its aspiration stroke, substantially.

3. The device of claim 1 in which means for placing a mark on the tissue adjacent the site of injection is supported on the second end of the elongated unitary tube spaced from the hypodermic syringe and being foreshortened from the length of the hypodermic needle by the desired depth of injection.

4. The device of claim 2 in which the means for restricting the rate of movement of the sliding valve is the combination of a hollow compartment affixed in the first end of the elongated unitary tube, said hollow compartment having a bleed orifice facing the head of the sliding valve, and a quantity of liquid filling the space between the head of the sliding valve and the hollow compartment, whereby the rate of movement of the sliding valve is controlled by the rate of bleed-through of the liquid into the hollow compartment.

5. The device of claim 2 in which the means for restricting the rate of movement of the sliding valve is a membrane of selected porosity affixed to the exterior wall of the elongated unitary tube covering the first port.

6. The device of claim 1 in which an annular medicated swab is affixed in a diametric plane to the second end of the main housing to both sterilize and to render taut the skin at the site of injection to facilitate needle insertion and to place a verification mark on the skin.

7. The device of claim 1 in which the source of compressed gas is a cylindrical canister having a puncturable end wall and being filled with pressurized gas, said canister being slidably supported in the main housing first end portion, a flexible impermeable membrane affixed to and sealing the main housing first end; and the manual means for releasing the gas pressure is a pointed perforator fixedly supported in the main housing first end portion with the point thereof proximate the puncturable end wall of the canister, resilient biassing means urging the canister away from the perforator except when said canister is manually translated into rupturable contact with said perforator.

* * * * *